(12) United States Patent
Bell et al.

(10) Patent No.: US 6,493,568 B1
(45) Date of Patent: *Dec. 10, 2002

(54) PATIENT INTERFACE SYSTEM (75) Inventors: Glenn B. Bell, Ellicott City, MD (US); Ronald B. Hicks, San Antonio, TX (US)

(73) Assignee: KCI Licensing, Inc., San Antonio, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 08/856,665

(22) Filed: May 15, 1997

Related U.S. Application Data (63) Continuation of application No. 08/642,591, filed on May 3, 1996, now Pat. No. 5,664,270, which is a continuation of application No. 08/277,253, filed on Jul. 19, 1994, now abandoned.

(51) Int. Cl.$^7$ .............................. A61B 5/00; A61G 7/00
(52) U.S. Cl. .............................. 600/323; 5/600; 5/609; 600/300; 600/333
(58) Field of Search ................................ 600/300, 301, 600/305, 323, 333; 128/DIG. 7; 5/600, 607, 609; 606/1

(56) References Cited

U.S. PATENT DOCUMENTS

| | | |
|---|---|---|
| 4,014,344 A | 3/1977 | Gutierrez |
| 4,183,015 A | 1/1980 | Drew et al. |
| 4,356,475 A | 10/1982 | Neumann et al. |
| 4,584,989 A | 4/1986 | Stith |
| 4,695,955 A * | 9/1987 | Faisandier .................. 600/300 |
| 4,768,241 A | 9/1988 | Beney |
| 5,259,365 A | 11/1993 | Nishikori et al. |
| 5,335,651 A | 8/1994 | Foster et al. |
| 5,375,604 A | 12/1994 | Kelly et al. |
| 5,390,382 A | 2/1995 | Hannant et al. |
| 5,473,536 A | 12/1995 | Wimmer |
| 5,527,289 A | 6/1996 | Foster et al. |
| 5,579,001 A | 11/1996 | Dempsey et al. ...... 340/870.01 |
| 5,579,775 A | 12/1996 | Dempsey et al. |
| 5,664,270 A | 9/1997 | Bell et al. ...................... 5/600 |

OTHER PUBLICATIONS

Colin Corporation, "One for ALL," date and place of publication unknown.
Hewlett–Packard Co., "HP–78580A Hp Careport Programmable SDN Interface," date and place of publication unknown.

(List continued on next page.)

Primary Examiner—Eric F. Winakur

(57) ABSTRACT

A patient interface system integral with a critical care bed for allowing the acquisition, analysis, display, and conveyance of patient-related data from a variety of transducers. The system is adapted to recognize and interpret each type of signal being received, despite the type and/or make of the particular transducers. The system is also adapted to simultaneously display data traces and representative readings from a variety of transducers simultaneously on a single screen detachably mounted to the bed. The display screen is pivotably mounted for ease of use and may be detached from the bed together with the main processor when the corresponding features are not desired. The bed is adapted with electronic connection sockets along each side of the patient surface to present convenient connections for patient transducer leads. The system has resident memory for storing data to enable trend analysis or downloading for patient data records. Bedside medical devices can either be connected to the device by cable connections or by use of wireless connections and is capable of controlling various medical devices related to the bed or patient, potentially including patient turn actuators, scales, inflation devices and others.

14 Claims, 3 Drawing Sheets

OTHER PUBLICATIONS

Hewlett–Packard Co., "HP CareVue 9000 Clinical Information System HP M1215A/M1216A." date and place of publication unknown.

Hewlett–Packard Co., "HP78730A CareVue 5000," date and place of publication unknown.

Hewlett–Packard Co., "HP CareVue 9000," date and place of publication unknown.

Hewlett–Packard Co., "HP 9000 Series 800 Reliable On–Line Computing Products," date and place of publication unknown.

Hewlett–Packard Journal, Oct. 1991, pp.6–13.

SpaceLabs, Inc., "Only One Patient Monitoring Company Can Make All These Connections," date and place of publication unknown.

SpaceLabs, Inc. "More Information. Better Information . . . ," date and place of publication unknown.

SpaceLabs, Inc., "Flexport," date and place of publication unknown.

* cited by examiner

PATIENT INTERFACE SYSTEM

RELATED APPLICATIONS

This Application is a continuation of Applicant's U.S. patent application Ser. No. 08/642,591 filed May 3, 1996, now U.S. Pat. No. 5,664,270 issued Sep. 9, 1997, which is a continuation of U.S. patent application Ser. No. 08/277,253 filed Jul. 19, 1994, now abandoned. By this reference, U.S. patent application Ser. No. 08/642,591 is hereby incorporated herein as though set forth now in its entirety.

BACKGROUND OF THE INVENTION

Field of the Invention

The present invention relates generally to medical devices and, more particularly, to specialized patient supports interrelated with medical data acquisition devices for optimally monitoring, processing, storing, displaying and utilizing patient data.

Background of the Invention

Patient data is often life-critical, especially in trauma and intensive care settings. It provides caregivers with objective information about the patient's condition. By comparing simultaneous data relating to a variety of strategic physiological parameters, caregivers can not only monitor and diagnose the patient's condition, but they can also evaluate the efficacy (and hence, value) of the patient's treatment.

With more technologies being utilized, the critical care room can easily become crowded, complicated and confusing. Each patient will typically have a vital signs monitor, a ventilator, multiple intravenous pumps, and half a dozen or so other ancillary life-supporting and/or therapeutic devices. The number grows as our understanding of medicine increases and more technologies become available. As for monitors alone, it is not uncommon to have your basic vital signs monitor plus another three or four specialized monitors crowded into any given room, with each unique monitor being mounted on a separate wheeled cart, often recording and displaying only a single vital sign. Patient temperature, blood pressure, EKG, heart rate, and $SaO_2$ (i.e., blood oxygen levels) are routinely monitored, as well as any number of additional vital signs or conditions that may be of particular interest with a given patient. A modern critical care room may also utilize a bedside computer terminal for patient charting. The caregiver brings up the patient's chart electronically to determine what procedures have been prescribed and updates it as appropriate. The overall result is a complex network of wires, transducers, displays, bulky cabinets, and device carts surrounding the critical care patient.

Use of patient-rotating beds and the like, such as those described in U.S. Pat. Nos. 5,142,719 and 4,763,463, presents particular difficulties in dealing with the complexity of critical care monitoring systems. Such beds inherently move a patient's body, typically rotating the body at least 90° from side to side. Since the patient's position is constantly moving relative to his monitors, the transducers and their cables must accommodate such movement. If a transducer is connected to a patient when the patient is rotated right, the transducer lead might be drawn taught as the patient is rotated to the left if the caregiver has not provided adequate slack in the line. The potential consequences are obvious—not only can transducers become dislodged or disconnected, but the wires can interfere with both equipment and caregivers.

Assuming all the leads remain properly connected, a caregiver then has the task of watching and mentally correlating each of the various displays with the patient to make decisions as to patient treatment. For instance, if a patient's blood pressure is down, the patient may need to be positioned in the Trendelenburg position, or if $SaO2$ levels are low, automatic ventilation or kinetic therapy may be prescribed. The long-recognized need in the critical care setting is to simultaneously correlate as much patient data with as many effective therapies as may be necessary to maintain and/or improve the patient's condition.

The need to occasionally transport a patient from one room to another further complicates matters. When transporting, each of the numerous pieces of wheeled equipment must simultaneously be rolled to the new location. Moreover, since virtually all the various technologies must first be disconnected from their wall power for transport, they must each have stand-by-power for transport, or be manually operated if possible. Many such stand-by schemes inherently risk loss of stored data in-transit. The result, too often, is to simplify matters by completely disconnecting the equipment during transport, when patient data is equally if not more important.

While others have long recognized the need to consolidate and simplify patient monitoring systems, competition amongst manufacturers tends to work against integration. Many manufacturers would rather set the standards for equipment interface, positioning themselves as the leader and forcing others to follow. They do not want other devices to utilize their information but would rather have customers be tied to them. They want customers to buy not only their transducers, but also their profit-laden monitors. Although some companies have established products which incorporate various devices in a transportable unit, the result too often is a seemingly insurmountable lack of communication between medical device transducers and monitors made by different competitors.

It is the overriding object of the present invention to address the problems and encumbrances of the prior art, providing a simpler, more convenient and efficient interface for medical data acquisition. This will enable caregivers to more efficiently monitor data, evaluate patient status, and adapt patient therapy, in virtually all circumstances. The particular applications range from basic lead connections, to pressure relieving mattresses, to lateral rotation beds.

SUMMARY OF THE INVENTION

Simplifying particular aspects of the invention, it basically comprises a critical care bed for supporting a patient wherein the bed serves as the information conduit between one or more transducers and their respective monitors and or other data recording devices. The bed itself also includes a processor for processing signals from the transducers. The transducers function conventionally, providing analog signals corresponding to sensed physiological characteristics of the patient. Conventional transducer leads and lead connectors are virtually inherent. The processor may also be conventional, although it is adapted for simplifying signal analysis and monitor recognition.

In one aspect of the present invention, the bed is provided with a universal port for receiving any one of a number of conventional lead connectors and linking the same to the processor. A plurality of linked alternative ports could be structured as another alternative. In such configurations, the processor is adapted to sense the signals received at the universal port (or from any one of the series of ports) and to "recognize" the source of such signals. With most digital signals, the data stream can be matched to the corresponding medical device. Source recognition for all analog signals and certain digital signals, on the other hand, will typically involve signal analysis of the signal on each pin of a transducer and then pin-mapping all the signals together. The signal analysis identifies the type of signal being coveyed on a particular pin—i.e., whether the signal is a steady, reference voltage or a fluctuating one sand, if fluctuating, whether it is fluctuating in a manner characteristic of any particular type of physiologic or environmental signal. Pin-mapping then correlates the signals of the various pins of a multi-pin transducer lead to distinguish an identifying profile and identify the corresponding signal source from the known bank of possibilities. With such a configuration, the system as a whole can then identify the make of multi-pin transducer signals and process the signals based on pre-defined data related to the particular signal source (i.e., the particular type and/or make of patient transducer).

For optimal convenience and minimal interference, a plurality of such universal ports may be positioned along opposite sides and/or at opposite ends of the patient support surface. Another aspect of the invention relates to a display system for displaying usable representations of received signals. Preferably, each signal is processed and then displayed in a graphic format relative to time, or a caregiver can selectively switch the display to digital display of current or time-averaged levels. The display is naturally linked with the processor, which in turn is adapted for interpreting and displaying data utilizing the display system. Uniquely, the display system itself is detachably mounted to the bed so that it can be detached in certain placements or at certain times. Preferably, such a detachable display is formed as a cartridge which includes not only the display but also the processor. Hence, whenever a patient, caregiver or facility desires to implement the features provided by the present invention, such a cartridge can be readily mounted and implemented on short notice without unnecessary replacement of the entire critical care bed. Such a display cartridge includes not only a slim-line processor but also a flat display screen to minimize bulk and to ease implementation. The cartridge is also adapted to allow the display screen to pivot relative to the bed for enabling convenient line-of-sight viewing by a caregiver at any location.

Another aspect of the present invention provides for integrating an SaO2 monitoring system with a display system that enables a caregiver to correlate SaO2 monitoring system with a display system that enables caregiver to correlate SaO2 with lateral rotation data. The result allows correlation between blood-oxygen levels and the therapeutic turning effect of the rotation. Such a system may also utilize a universal port as referenced previously, and may be logistically linked with the critical care bed controls to modify the therapy protocol in response to the current and or historical SaO2 levels. Eventual concepts of incorporating self regulating systems of patient care or physician approved suggestions of a smart system could be included. Axial routing of data lines from the transducers to the detachable processor and thence to the respective external monitors not only renders a convenient data conduit, but also helps eliminate potential for taught-line problems.

Many other objects, features and advantages of the present invention will be evident to those of ordinary skill in the art from the following more detailed description of presently preferred embodiment, particularly when considered in light of the accompanying drawings and the appended claims.

BRIEF DESCRIPTION OF THE DRAWINGS

Although the scope of the present invention is much broader than any particular embodiment, a detailed description of certain preferred embodiments follows together with illustrative figures, wherein like reference numerals refer to like components throughout, and wherein.

DETAILED DESCRIPTION OF THE PREFERRED EMBODIMENT

Figure 1:
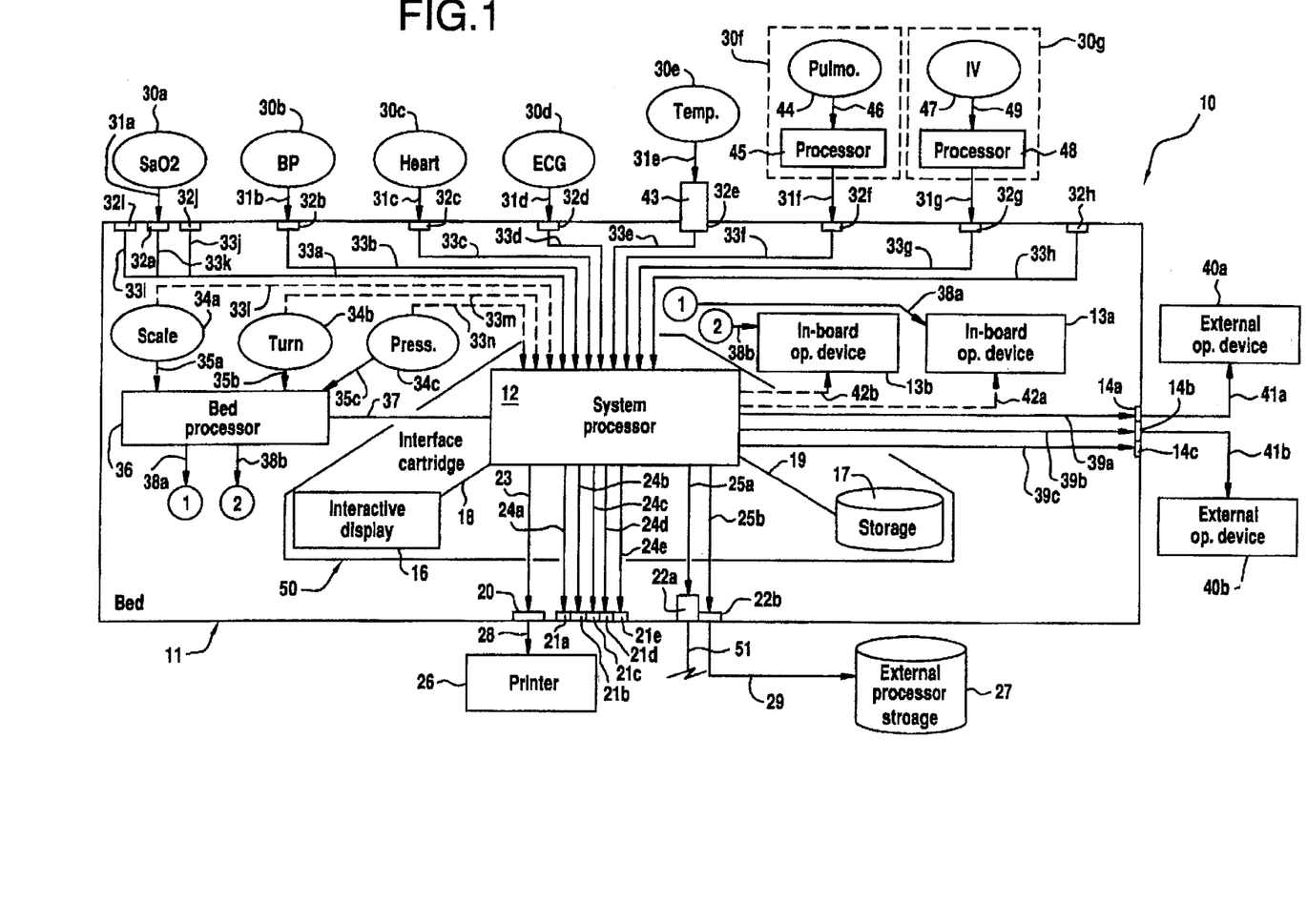
FIG. 1 shows a schematic view of a patient interface system 10, which is a preferred embodiment of the invention.

Referring to FIG. 1, there is shown a schematic view of a patient interface system designated generally by the numeral 10. Although the present invention may be embodied in a wide variety of different types of systems, patient interface system 10 is an illustrative, preferred embodiment. The system 10 generally includes a critical care bed assembly 11, along with several detachable components linked electronically to bed assembly 11. The detachable components illustrated in FIG. 1 include transducers (and transducer systems) 30a–30g, external operative devices 40a–40b, printer 26, communications system 51, and external operative devices 40a–40b, printer 26, communications system 51, and external processor storage 27. Bed 11, itself, generally includes a central processing unit 36, integral sensors 34a–34c, in-board operative devices 13a and 13b, numerous electrical connection ports and electrical connections which will be described further herein, and interface cartridge 50.

Figure 2:
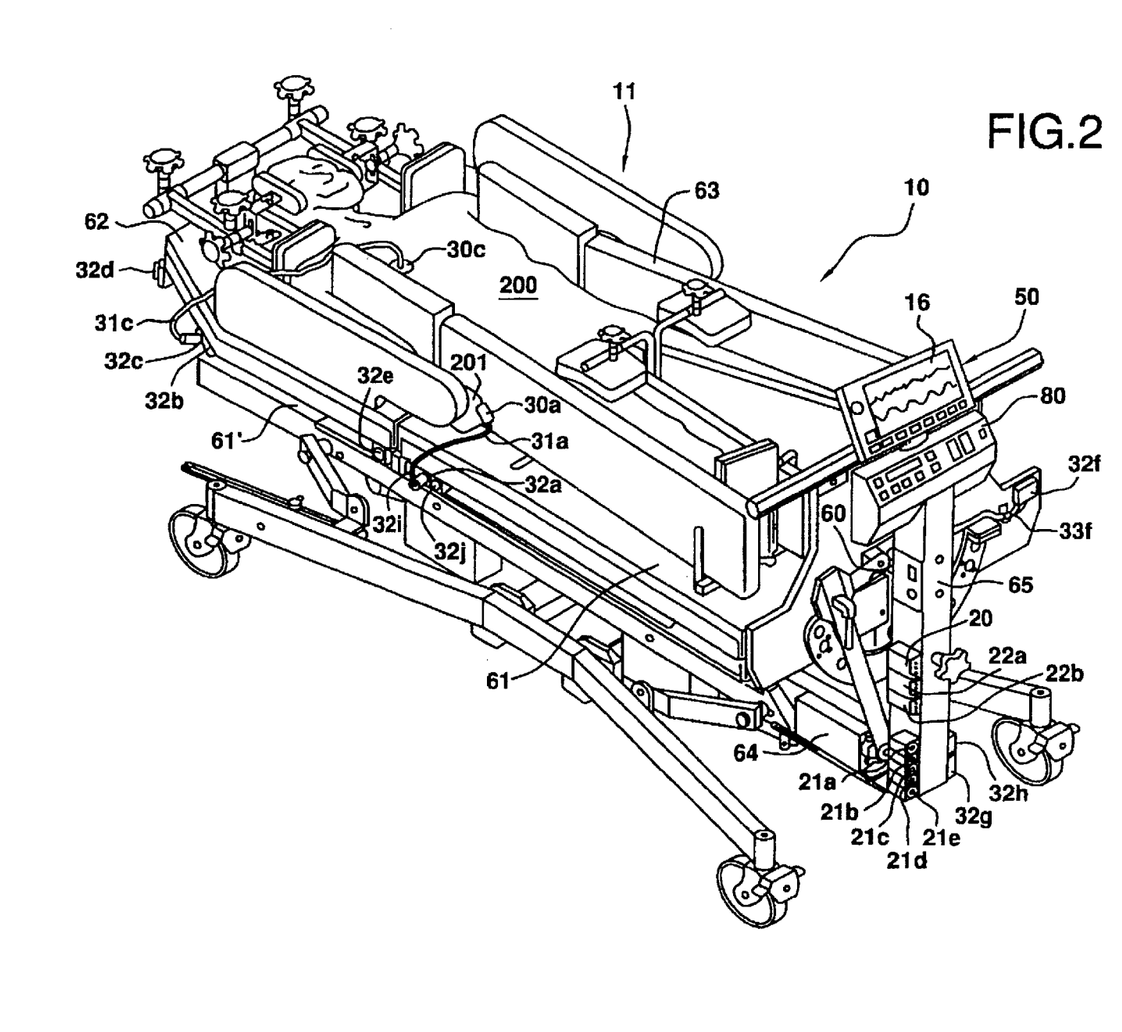
FIG. 2 shows a bird's-eye perspective view of a critical care bed assembly 11 adapted to implement the patient interface system 10 shown schematically in FIG. 1.

Referring to FIG. 2, there is shown a bird's-eye perspective view of critical care bed assembly 11 of the preferred embodiment. Bed assembly 11 is essentially a Roto Rest Delta bed presently commercialized by KCI Therapeutic Services, Inc. of San Antonio, Tex., with certain adaptations. Particularly, the Roto Rest Delta bed of bed assembly 11 is adapted with interface cartridge 50 and a variety of transducer ports 32a–32j, monitor ports 21a–21e, printer port 20, and communication ports 22a and 22b, as well as numerous related electrical connections (such as line 33f and many others that are not shown) as referenced generally in connection with FIG. 1.

Interface cartridge 50 is a detachable cartridge that serves in part to facilitate the interface between transducers such as transducers 30a–30g and 34a–34c and the user. In simplest forms, interface cartridge 50 facilitates such interface by providing a data storage and/or display device for the benefit and convenience of patient caregivers. In other respects, interface cartridge 50 uses received data to modify the operation of inboard operative devices 13a and 13b and/or external operative devices 40a and 40b.

Figure 1A:
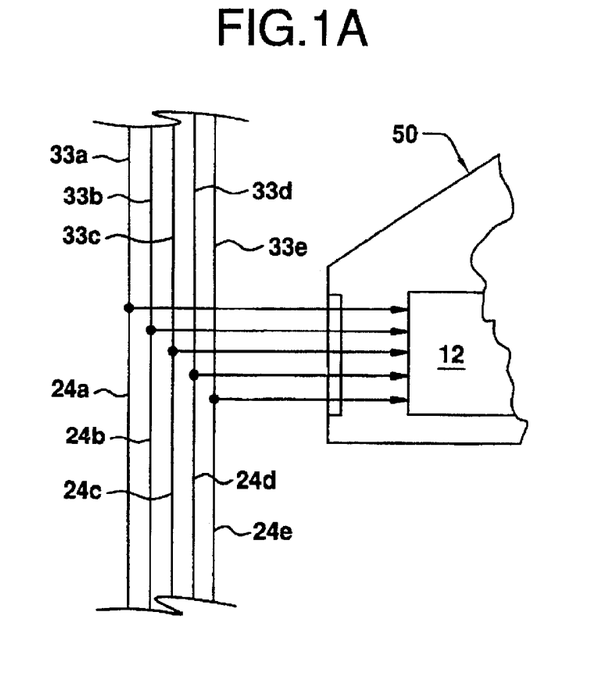
FIG. 1A shows a more accurate detailed schematic view of general relationship between lines 33a–33e, interface cartridge 50 and lines 24a–24e.

Bed assembly 11, as a whole, provides a convenient conduit for conveying signals received from transducers 30a–30e to remote monitors (not shown) that may be linked to ports 21a–21e. Ports 21a–21e may be adapted as desired, but it is presently preferred that they be of such construction that would facilitate connection of leads like leads 31a–31e, respectively. In this fashion, bed assembly 11 in concept can be simply interjected between transducers 30a–30e and the monitors that are traditionally used with such transducers, all without interrupting or altering the signal between transducers 30a–30e and their corresponding monitors. When interface cartridge 50 is detached from bed assembly 11, signals carried by lines 33a–33e are still conveyed to ports 21a–21e. A more detailed representation of the relationship between lines 33a–33e, interface cartridge 50, and lines 24a–24e is shown in FIG. 1A.

To help convey a more complete understanding of all the various aspects of the present invention, patient interface system 10 is described with specific numbers and identities of multiple components. For instance, there are seven specific external transducers, three internal transducers, two in-board operative devices, and two external operative devices. Some of the multiple components will be described with specific detail while others (such as the external operative devices 40a–40b) may be left generic. For purposes of this description, both the illustration and description of many of these components is also greatly simplified. Blood pressure transducer 30b, for instance, may be described only as a transducer with an electronic signal related to the blood pressure of patient 200, whereas one of ordinary skill in the art would recognize that a typical noninvasive blood pressure transducer is inoperative without an inflation cuff and related components and that the signal from such a transducer would actually be either a comprehensive digital signal or multiple analog signals which could be interpreted in combination to determine the patient's blood pressure. This description will, hence, be best understood by those of ordinary skill in the art who, with reference to presently available technology, would recognize and understand such simplifications. The selection and details related to such multiple components generally should not be read as limitations on the scope of the present invention, unless such details are required by the claims appended hereto which define the scope of this invention, once properly construed.

A variety of patient transducers are commonly utilized in the critical care settings. Ten such transducers are represented in FIG. 1—seven "external" transducers 30a–g and 34a–c serve a variety of purposes in sensing various characteristics related to a patient supported on bed 11. Transducer 30a is an SaO2 transducer for sensing the blood-oxygen saturation levels of the patient. Transducer 30b is a blood pressure transducer for sensing the blood pressure of the patient. Transducer 30c is a heart rate transducer for sensing the heart rate, or pulse, of the patient. Transducer 30d is an ECG transducer for sensing an electrocardiogram signal of the patient. Transducer 30e is a core temperature transducer for sensing the core temperature of the patient.

Both transducers 30f and 30g can be considered strictly as transducers but are actually transducer systems that include an independent processor (and other components) together with a transducer. Transducer 30f, for instance, is actually a patient ventilator that includes one or more pulmonary monitor transducers 44 linked to processor 45 by lead 46. Processor 45 processes the signal from transducer 44 to produce a more comprehensive signal representative of the patient's breathing activity. Processor 45 then transmits that more comprehensive signal through lead 31f Transducer 30g is a drug or IV infusion pump unit that likewise includes a transducer 47 and processor 48 that work to monitor the volume of fluid being infused to a patient and to transmit a corresponding signal through line 31g.

Figure 1B:
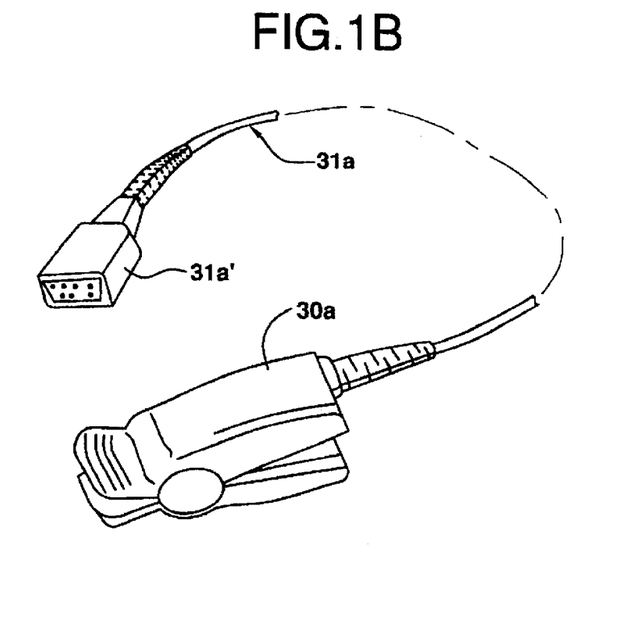
FIG. 1B shows a partial view of an illustrative transducer lead 31a that may be used in conjunction with the preferred embodiment shown in FIG. 1.

Each of transducers 30a–g are conventional, selected from those that are well known in the industry, through a variety of manufacturers. Though well known, many such transducers are commonly dedicated to an independent monitor but are typically detachable from said monitors, leaving the transducer 30 itself and its corresponding lead 31. The leads 31, operatively connected between the corresponding transducer 30 and connection port 32, are simply electrical leads of appropriate construction—that is, appropriate for communicating the electrical signals from the transducer 30 to a processor that is adapted to interpret such signal and, hence, monitor the intended physiological or environmental condition sensed by transducer 30. Although not shown in FIG. 1, each such lead 31' is provided with a conventional lead connector 31' at its distal end (i.e., the end of lead 31 which connects to the corresponding connection port 32). (For purposes of this description, let it be understood that any reference to one of transducers 30a–g as "transducer 30", and any like references to other components such as transducer leads 31a–g and the like, are intended to be generic references which should apply to any of the transducers 30a–g or the like.) FIG. 1B depicts one such lead connector 31a' at the distal end of lead 31a', as an example. Leads 31a–g may also include other coupling connections as are conventional.

Bed 11 is provided with a plurality of transducer connection ports, or sockets, 32a–32j for receiving individual leads 31a–31g of transducers 30a–30g and enabling electronic communication between such transducers 30a–g and interface cartridge 50 as well as remote monitor ports 21a–21e. Several of ports 32a–32j are unique to particular types of lead connectors, despite the fact that they are all represented the same in FIG. 1. For instance, transducer port 32b has a construction adapted to operatively receive a conventional blood pressure transducer lead 31b, which has a certain number of pins arranged in a certain geometry of a certain size. For simplicity, each of ports 32a–e are of the same construction, geometry, etc., as the ports already commercially available which are adapted to receive transducer leads 31a–31e. This works best when all of the transducer leads to be connected to a particular port are the same. A leading blood pressure transducer manufacturer, for instance, is Colin Medical of San Antonio, Tex., and port 32b is adapted for operatively receiving the conventional leads provided with their blood pressure transducers. Hypothetically, it may also be that all competitors for a given type of transducer use the same transducer lead, in which case selection of the construction of port 32 will be an easy decision. In another case, there may be several popular alternative transducers of the same general type, and each separate manufacturer may have its own unique type of transducer lead. System 10 addresses such a situation by providing a universal port, which is a transducer port (or series of ports) that will interface with a variety of different transducer leads.

In FIG. 1, one representation of the universal port concept relates to the series of sockets 32a, 32i and 32j for receiving the SaO2 transducer lead 31a. The SaO2 monitoring market is representative of a market where the transducer leads for SaO2 transducers made by different manufacturers are likewise different and unique. To address this, rather than having a single socket for receiving all SaO2 transducer leads, there is a series of three sockets 32a, 32i, and 32j dedicated for this purpose. As shown in FIG. 2, in actual implementation, such series of ports 32a, 32i, and 32j are oriented immediately adjacent one another in a location proximate to the hand 201 of patient 200, where many SaO2 leads are adapted to be connected. Hence, a caregiver connecting an SaO2 lead 31a to bed assembly 11 can know to always go to the same general location to connect the lead 31a, regardless which manufacturer made the particular lead 31a being used for a particular patient 200. The socket 32a is adapted to receive the transducer lead made by one manufacturer, such as a Nellcor lead; the socket 32i is adapted to receive the lead made by another manufacturer; and the socket 32j is adapted to receive the lead manufactured by yet another manufacturer or category of manufacturers.

Another manner of providing a universal port to address the stated need is represented in connection with transducer port 32e. Rather than having multiple sockets for a single type of transducer, a single temperature transducer port 32e is provided for multiple makes of temperature transducer leads 31e. The port 32e is particularly adapted to receive the most popular, or most preferred, type of temperature transducer lead, and adapter 43 is utilized to enable connection to the transducer lead of a less popular, or less preferred, type of transducer lead. A plurality of adapters 43 may be made available if it is desired to have more than two basic types of transducer leads 31e connectable at the same port 32e.

Transducer ports 32f–32h are universal in the sense that they are each of the standardized RS-232 format. Hence, being of the standardized format, any transducer (or transducer system) using a transducer lead of the RS-232 format can be connected to any of ports 32f–32h.

Although eight connection ports 32a–32j are shown (considering sockets 32a, 32i & 32j are a single port), only seven transducers 30a–g are illustrated. An additional transducer may be connected to the remaining connection port 32h, as desired.

Electronic communication lines 33a–33k are conventional lines that electronically link transducer ports 32a–32j to interface cartridge 50 so that cartridge 50 receives any signals that are received at ports 32a–32j. Such construction is generally straight forward—if transducer port 32b is a 10-pin port, then electrical connection 33b is an electrical connection capable of transmitting at least 10 parallel signals, each correlated to a separate pin of transducer port 32b. Conventional ribbon cables and/or conventional coaxial cables are preferred for each of lines 33a–33h, and others. The only particular complication relates to the series of sockets 32a, 32i and 32j, wherein corresponding electrical leads 33k, 33i and 33j merge into a single electrical lead 33a. Any conventional means of merging such lines, as will be evident to those of ordinary skill in the art, is suitable for this purpose; however, it should be noted that one of ports 32a, 32i and 32j may have a different number of pins than the others. In such a case, the lines 33k, 33i and 33j can still each have the same number of conductors, even though some of such conductors may not be required for each of the different transducer sockets 32a, 32i and 32j. For example, if socket 32a has ten pins, socket 32i has eight pins, and socket 32j has four pins, then a ten-conductor line will be used for each of lines 33a and 33i–k, with some conductors not being used for sockets 32i and 32j.

The integral transducers 34a, 34b and 34c are also electronically linked with interface cartridge 50. Such link, in the preferred embodiment, is directed through the central processing unit 36 of bed 11. More particularly, transducers 34a, 34b and 34c are linked to bed processor 36 by transducer leads 35a, 35b and 35c respectively. Bed processor 36 then processes the signals received through transducer leads 35a, 35b and 35c in the same manner as though interface cartridge 50 were not a part of bed assembly 11. Bed processor 36, for reference, is the control unit in the presently commercialized version of the Roto Rest Delta bed, and is mounted within the enclosure of control panel 80. Having processed signals received from leads 35a, 35b and 35c, processor 36 then transmits a representative signal through interprocessor link 37 to interface cartridge 50. Releasable connections such as at ports 32 are not shown in lines 35a–35c, both for simplicity and as they are not required, although they may be utilized for convenience in servicing bed 11.

In an alternative embodiment, transducers 34a–34c may communicate directly with interface cartridge 50 through lines 33l–33n (shown in hidden line in FIG. 1). In such alternative, system processor 12 is adapted with the appropriate code to process the signals received through leads 33l–33n. Rather than having bed processor 35 control the operation of inboard operative devices 13a and 13b, as in the preferred embodiment, such alternative embodiment may also have interface cartridge 50 control the operation of inboard operative devices 13a and 13b directly via electrical connections 42a and 42b, respectively (also shown in hidden line).

Transducer 34a is a patient weight transducer for sensing the weight of the patient. The weight transducer 34a is a commercially available transducer such as the LVDT-type transducer described in U.S. Pat. No. 4,793,428, dated Dec. 27, 1988. More particularly, the weight transducer 34a in the preferred embodiment is the LVDT-type transducer which is an integral component of the commercially available version of the Roto Rest Delta bed included in bed assembly 11. Other conventional types of weight transducers may also be used, such as load cells.

Transducer 34b is an angle sensor for sensing the degree of lateral rotation of a patient supported on bed 11. Such turn angle sensor 34b is an integral component of the commercially available version of the Roto Rest Delta bed included in bed assembly 11 in the preferred embodiment. The Turn angle sensor 34b in the preferred embodiment is a potentiometer (not shown) mounted in association with the central rotational shaft 60 (shown in FIG. 2) about which the patient platform 61 of bed assembly 11 is adapted to rotate. Analog signals from such turn angle sensor 34b (i.e., the potentiometer) are processed by bed processor 36, the digital signal for which is then tapped from the control board of the bed processor 36 to cartridge 50. Appropriate connections to bed processor 36 will be evident to those of ordinary skill in the art.

The turn angle sensor 34b is closely related to inboard operative device 13b, which is also integrated in the presently available Roto Rest Delta bed in the preferred embodiment. In-board operative device 13b is actually a group of devices including a drive motor mechanically linked for effecting lateral rotation of patient 200. More particularly, inboard operative device 13b includes a drive motor 64 which is linked to impart rotation to the patient support platform 61 so that it will oscillate from side to side in a predetermined arc. For a further understanding of operative device 13b, refer to U.S. Pat. Nos. 4,175,550 and 4,763,643 dated Nov. 27, 1979 and Aug. 16, 1988, respectively.

In an alternative embodiment, inflatable turning bladders may be utilized to achieve the lateral rotation of patient 200, such as described in U.S. Pat. No. 5,003,654 dated Apr. 2, 1991, and Applicant's co-pending U.S. patent application Ser. No. 08/241,075 filed May 9, 1994. Although referenced as a turn angle sensor, transducers utilized in such alternative embodiment may actually be pressure transducers, with the pressure sensed being translated to determine the approximate angle of rotation of a patient supported thereon. Other variations of the turn angle sensor 34b are described in said co-pending application.

Unlike transducers 34a and 34b, which are presently integrated in commercially available versions of the Roto Rest Delta bed, transducer 34c is an interface pressure sensing device for sensing the interface pressure between the skin of patient 200 and the mattress on which patient 200 lies. The construction of such an interface pressure sensor, together with reference to an inflatable patient supporting system (a variation of which may be integrated in conjunction with the foam mattress of the Roto Rest Delta bed of bed assembly 11), is described in U.S. Pat. No. 4,797,962 dated Jan. 17, 1989. More particularly, a preferred interface pressure sensor is described in conjunction with FIGS. 4 and 5 therein. Other interface pressure sensors may be evident to those of ordinary skill in the art. Similar to the relationship between turn angle sensor 34b and inboard operative device 13b, processor 36 may be adapted to control the operation of inboard operative device 13a in response to signals received from interface pressure sensor 34c.

More particularly, inboard operative device 13a in the illustrated embodiment includes a valve servo motor for controlling the inflation pressure of an inflatable patient support that may be utilized in conjunction with the Roto Rest Delta bed patient surface. Specifically, if interface pressure sensor 34c senses interface pressures exceeding acceptable levels (preferably capillary closure pressure), bed processor 36 is adapted to control inboard operative device 13a to generally reduce the airflow to such inflatable patient surface. The details of integrating inboard operative device 13a with the Roto Rest Delta bed may not be completely understood at present, although one of ordinary skill in the art will be able to achieve such integration without undue experimentation. One attempt to do so would be to remove the foam mattress surface 62 from the Roto Rest Delta bed and replace it with any of the various inflatable mattress overlays that are presently available on the market, such as that marketed as the "DynePulse" available through Kinetic Concepts, Inc. of San Antonio, Tex. Some adaptations to such surfaces (as will be evident to those of ordinary skill in the art) are necessary in order to allow operative mounting of the various foam packs 63 and the like which form part of the patient supporting system above mattress 62 of the Roto Rest Delta bed. The blower unit for such inflatable mattress overlay can be secured to the underside of the patient supporting platform 61 to further facilitate such an embodiment. Rather than a valve servo-motor (as previously described), inboard operative device 13a may also be a variable speed blower which could form part of the blower unit for such inflatable overlay. Regardless of whether inboard operative device 13a is a variable speed blower or a valve-servo motor, its purpose is to control the inflation pressure of the inflatable mattress overlay by controlling the flow of inflation air provided thereto.

In use, bed 11 allows a caregiver to simplify and consolidate monitors linked to patient 200 in a manner of great convenience. With any of the various transducers 30a–30g, if the transducer is deployed in its simplest form (i.e., without its corresponding monitor or another dedicated processor), signals from the transducer will typically be analog signals. For simplicity, each of transducers 30a–e are described as though they do not include a processor and, hence, transmit analog signals; and each of the transducers 30f and 30g are described as though they include microprocessors and, hence, transmit digital signals. The illustrated selection of which transducers include microprocessors and which do not, however, is mostly arbitrary in the illustrated embodiment. This description should, therefore, be read with an understanding that most transducers may be linked to bed assembly 11 with or without their monitors, while still falling within the scope of most aspects of the present invention.

In the preferred embodiment, a conventional analog-to-digital (A/D) converter is used to convert the analog transducer signals to digital, for processing by an appropriate microprocessor. Processor 12 preferably includes such an appropriate microprocessor as well as the A/D converter, amplifiers, filters, and such other circuitry as is appropriate for processing signals received through electrical connections 33a–33e (and 331–33n, if applicable) to produce a digital signal capable of being processed through the microprocessor.

As an alternative to such conventional A/D converter and related circuitry, another embodiment includes an analog input module marketed under the designation Datascan 7021 with Firmware V2.0 (Measurement Systems Limited, of Newbury, Berkshire, England). Such module and firmware, when operatively connected, not only converts multiple analog signals to digital, but also multiplexes the resulting signals and transmits them through a single RS-232 line. Hence, in the alternative embodiment, such a module is used in (or in conjunction with) processor 12 to facilitate processing of signals from the various transducers 30a–30j that can be linked to processor 12.

Controller 12 is adapted to control the overall acquisition, processing, storage, display and transmittal of data related to transducers 30a–30g and 34a–34c. In general, such control can be considered in seven categories: device initialization, screen set-up, data acquisition, data storage, data display, and data transmission. Device initialization in the preferred embodiment is a two-step process—step one being source identification, and step two being initialization of data acquisition parameters based on the source identification. Although the user of assembly 11 may input the information which identifies the source of a particular signal, source identification in the preferred embodiment is a process by which processor 12 processes signals from lines 33a–33n to the point of recognizing the source based on comparison with known characteristics of signals from the possible sources. The processing also involves interpreting the signal to determine physiological data related to the patient and/or the patient environment, based on the source identification. In some embodiments, controller 12 is also adapted to control the operative devices 13a–13b and 40a–40b.

The source recognition process of processor 12 involves a variation of one of two concepts. In connection with most digital signals received through lines 33f–33h, the source identification simply involves a conventional "handshaking" routine known to those of skill in the art. In conjunction with either analog signals or unidentifiable digital signals (such as those from an analog input module) received through lines 33a–33h, the source identification process includes both signal analysis and pin-mapping. With analog signals, for instance, certain transducers characteristically transmit predictable, steady voltages on specific conductors and predictable signals on specific other conductors of its line. With a digital signal, the data stream on certain lines may be unique for a given make of device. The signal analysis process (including conventional processes such as band-pass or other frequency analysis, template matching, or other conventional techniques) identifies the type of signal being conveyed on a particular pin of a given transducer 30—i.e., whether the signal is a steady, reference voltage or a fluctuating one and, if fluctuating, whether it is fluctuating in a manner characteristic of any particular type of physiologic or environmental transducer signal. Accordingly, processor 12 can observe and distinguish the characteristics of the signals received on each of the multiple conductors. In other words, processor 12, either through analog or digital processing, distinguishes the signals from the data stream in each conductor. Thus, for a five-conductor line, the signal profile might comprise the frequency of the five signals corresponding to the five conductors.

The pin-mapping process of processor 12 then correlates the signals of the various pins of a multi-pin transducer lead 31 to produce an identifying profile that is characteristic of the signal transmitted on a given transducer lead 31. The signal profile for each line 33a–33h is then compared by processor 12 to known signal profiles corresponding to known types and makes of transducers. For instance, a transducer signal from a given make of a particular type of transducer may characteristically include signals of specific frequencies on specific pins of a ten-pin transducer lead, and processor 12 can identify whether a given signal correlates with such signal profile by matching it with profiles stored in its memory 17, which were developed to be characteristic of all the possible signal sources. With such a configuration, the system as a whole can then identify the make of multi-pin transducer 30 based on the signal transmitted from the transducer 30. With the source identified, control 12 then processes the signals received from the respective transducer 30 based on pre-defined data related to the particular signal source (i.e., the particular type and/or make of patient transducer). Thus, processor 12 is adapted to process and filter a received signal to distinguish its components and correlate the same with an identifying profile in order to recognize the type and make of the transmitting transducer. Having identified a profile, processor 12 then processes the signal in whatever manner the identified profile should be processed, based on instructions in its memory corresponding to the identified profile. Having matched a signal with a Nellcor profile, for instance, processor 12 then processes the signal in whatever way Nellcor signals should be processed to yield usable data for display and/or storage.

Once processor 12 has completed its device initialization process, it then operates to complete the other aspects of its control—namely, screen set-up, data acquisition, data storage, data display, and data transmission. The screen set-up is conventional, for setting up the format to be displayed on screen 16 either in graphic form, digital (i.e., meter-type) form with a selectable number of decimal places, or a combination thereof The data acquisition process is also conventional—essentially polling the initialized devices based on the known information about such devices. Data storage involves creating an appropriate data file and storing data in an appropriate format in such file or files. Both the data display and data transmission aspects are conventional subroutines as are wellknown in the industry.

As has been described, the signals are conveyed from the respective transducers 30a–30g through the corresponding transducer ports 32a–32j and related lines 33a–33k. The ports are secured in place to the underside of the patient supporting platform 61, preferably at strategic locations around its perimeter 61. Although not shown in FIG. 2, lines 33a–33k extend from the respective ports 32a–32j towards the central region of patient platform 61 and, thence, to the foot-end column 65 of bed assembly 11. More particularly, lines 33a–33k are positioned to pass from the underside of platform 61 to column 65 in close proximity to rotation shaft 60. Such passage may either be through a hollow center of shaft 60 or simply positioned in close proximity thereto so that lines 33a–33k require less slack and are less susceptible to being drawn taught or damaged during rotation of platform 61. Lines 33a–33k are allowed to pass to the interior of column 65 through an opening (not shown) therein. In this way, lines 33a–33k remain relatively out of-the-way and are less susceptible to being damaged. As will be evident to those of ordinary skill in the art, within the interior column 65, lines 33a–33k are thence directed to their respective destinations through appropriate openings in the walls of column 65.

Display 16 is a slim-line, flat screen of a relatively large size. In the illustrated embodiment, such screen is an LCD screen roughly eight inches wide and five inches in height, which is formed integral with cartridge 50. The user (or caregiver) is able to interface with the display 16 via control buttons on the bed 11 control panel in an alternative preferred embodiment, although the illustrated embodiment is contemplated to include an interactive screen constructed in a manner which will be evident to those of ordinary skill in the art. Such an interactive screen might include either an integral touch screen or an integral membrane panel providing membrane witches immediately adjacent the LCD portion of display 16. The display driver and related software system are preferably on the Windows-type format, incorporating variable size and the ability to customize viewing parameters. Pull-down menus with icons, help screens, and hierarchical structure are used, to almost eliminate the need for an operation manual. In one contemplated embodiment, although the details have not been fully worked out, display 16 and processor 12 are adapted such that a care-giver (or user) uses display 16 to select which transducers are to be deployed for a given patient at a given time. The transducer could already be in position relative to the patient, and when the care-giver selects the transducer, control 12 modifies bed assembly 11 to energize the transducer and/or interpret the signal from such transducer.

Cartridge 50 is detachably mounted at the foot end of bed 11 atop control panel 80, which itself is integrally formed with column 65 at the top thereof. Cartridge 50 in the illustrated preferred embodiment is an integral construction that includes controller 12, display 16, memory components 17, and related connections for operatively inter-relating the same components. As will be evident to those of ordinary skill in the art, such a cartridge 50 can be provided on a customized basis through companies such as Carol Touch of Roundrock, Texas. In the illustrated, preferred embodiment, cartridge 50 more particularly includes a touch screen display 16, a controller 12 marketed under the designation "Cardio-386) (available through S-MOS Systems, a Seiko Epson affiliate of San Jose, Calif.) and conventional memory device 17 for use therewith. The Cardio-386 controller is a controller compatible with the IBM PC AT that is condensed to a PCMCIA card. With such construction, cartridge 50 integrates each of the illustrated components in a compact yet highly-functional unit.

The mounting of cartridge 50 is such that display screen 16 swivels about both vertical and horizontal axes to enable viewing. The horizontal swivel axis is fixed relative to display screen 16 to prevent display 16 from being tilted side to side. Hence, display screen 16 may be viewed from any direction but is not tiltable sideways so as to help minimize confusion in interpreting the display screen 16. Although the particular details and make of cartridge 50 and its mount atop column 65 are not particularized, such details will be evident to those of ordinary skill in the art. As an alternative, albeit simpler arrangement, a separate personal computer may be utilized in conjunction with a conventional flat screen mounted with any of the many available mountings for such screen atop column 65 or at any other convenient location on bed 11. One such suitable, preferred alternative is to utilize a "PLANAR" electroluminenscent monitor (made by PLANAR Systems, Inc. of Beaverton, Oreg.), model ELM-VGA. In such alternative, the monitor is mounted with a suitable mount to be clamped on to the bed and be used in conjunction with a conventional personal computer, preferably of the laptop notebook style. Appropriate data and power lines are employed in such fashion as will be evident to those of ordinary skill in the art. Acceptable mounting devices which can be screwed to an appropriate location on bed 11 are also available through PLANAR Systems, Inc. of Beaverton, Oreg.

In addition, processor 12 may be linked by connection 25 to a hospital's nursing station, an on-line charting system, a physician's office or to any desired remote location. The communication link for such alternatives may be via a network or some form of external memory, i.e., external processor storage 27, or may connect in whatever manner is appropriate for a given application. One preferred type of link is by way of communication system 51. Communication system 51, in the preferred embodiment, includes a conventional modem together with such hardware, modem drivers, and other software code that is conventionally used to facilitate communication of data by way of modem. Such software, for instance, may include the popular "ProComm" version 2.4.2, available through Datastorm Technologies, Inc. of Columbia, Mo. Communications system 51 may, in an alternative embodiment, utilize a radio-frequency (RF) module or other telemetry system to simplify connections as desired. The desirability of such RF, modem and/or telemetry capability depends on the circumstances. For instance, applications in the home environment may be particularly suited for utilization of a modem link to a nurse's station or physician's office. Processor 12 is preferably adapted with software to periodically and/or continuously down-loan patient data to the hospital system through either line 29 or communication system 51, in a conventional manner.

Although slightly different than the illustrated embodiment, one current embodiment presently reduced to practice in a preferred format includes a conventional 486 microprocessor. The microprocessor is equipped with data acquisition software marketed under the name "LabTech Notebook", distributed by LabTech of Wilmington, Mass. To facilitate the data acquisition, an analog-to-digital (A/D) converter circuit commercially available through CyberResearch, Inc. of Branford, Conn. under the trade designation "Cydas" is used. This combination is then operatively linked (or contemplated to be linked) to the following monitors: a Baxter-Edwards Explorer continuous cardiac output device (Baxter Health Care Corp., Edwards Division, of Irvine, Calif.), a Pfizer Paratrend 7 Intravascular blood-gas monitor system (Pfizer Biomedical Sensors of Malvern, Pa.), a Siemens Servo 900C/D ventilator (Siemens Medical Electronics, Inc. of Mass.), a BiCor physiological monitor CP-100 (BiCor monitoring systems of Irvine, Calif.), a BSM-8300 Nihon-Kohden ICU monitor (Nihon-Kohden America, Inc., of Irvine, Calif.), a Roto Test Mark I Delta (available through Kinetic Concepts, Inc., San Antonio, Tex.), a Nellcor pulse oximeter (Nellcor Inc. out of Hayward, Calif.). An alternative embodiment might replace one or more of these monitors such as replacing the Nihon-Kohden America, Inc. (out of Irvine, Calif.) monitor with a Hewlett-Packard Company (of Andover, Mass.) Hewlett-Packard Model 78342A monitor. Another contemplated embodiment is to use a Protocol ProPaq monitor (ProtocolSystems, Inc., of Beaverton, Oreg.) as a transducer system. To facilitate such alternative, the Protocol unit is preferably adapted as an "ACUITY" package by the Protocol manufacturer, so that more usable signals can be transmitted to processor 12. It is thought that similar types of modifications can be made to an IVAC Space-Saver IV Pump (IVAC Corporation, San Diego, Calif.) to obtain usable signals for monitoring IV infusion levels. If not, other IV pumps such as the Gemini PC-1 (Imed Corporation, of San Diego, Calif.) are believed to have RS-232 data ports as a standard feature. In use, the software package is utilized to acquire and store the data and display it on a conventional computer screen and graphical and/or meter form, with multiple traces on the same screen. The information may be input into the system either through the A/D converter (i.e., the signal processor) or directly through the computer's COM ports.

Each of the U.S. Patents and pending patent applications referenced in the foregoing descriptions is incorporated herein by reference as though set forth here in its entirety.

Although the present invention has been described in terms of the foregoing preferred embodiments, this description has been provided by way of explanation only and is not to be construed as a limitation of the invention, the scope of which is limited only by the following claims.

We claim:

1. A patient interface system comprising:

a bed for supporting a patient, said bed comprising a universal port for operatively receiving any one of a plurality grouping of conventional transducer leads, each member of said plurality grouping being adapted to cooperate with a conventional transducer to provide a signal related to a sensed physiological characteristic of the patient;

a processor linked in communication with said universal port, said processor being adapted (a) to receive a signal from said port, (b) to process the received signal to distinguish an identifiable component of the received signal, (c) to correlate such identifiable component with an identifying profile, and (d) to process the received signal based on data related to the identifying profile.

2. The patient interface system of claim 1, further comprising;

a display system for displaying a representation of signals processed by said processor relative to time, said display system being operatively linked with said processor, wherein said processor is adapted to interpret and display the processed signals utilizing said display system.

3. The patient interface system of claim 2, wherein said display system is pivotally mounted to said bed.

4. The patient interface system of claim 2, wherein said display system is detachably mountable on said bed and is pivotable relative to said bed when so mounted.

5. The patient interface system of claim 4, further comprising a detachable cartridge including said processor and said display system, wherein:

said processor is a slim-line processor;

said display system includes a flat display screen; and said cartridge is adapted such that, when the cartridge is connected to said bed, the display screen is pivotable about a horizontal axis relative to said bed for enabling viewing of said screen by a patient caregiver.

6. The patient interface system of claim 1, wherein:

said bed includes an elongated patient supporting surface having opposite lateral sides; and said universal port is positioned, along with a plurality of additional ports, along opposite sides of said patient surface.

7. A patient interface system comprising:

a bed for supporting a patient;

an electronic connection port adapted to operatively engage a blood-oxygen transducer connected to the patient and to receive a signal related to the blood-oxygen level of the patient from the transducer;

a display screen; and a processor for processing said received signal, said processor being electronically connected to said port and to said display screen, said processor being adapted to interpret and display the patient's blood-oxygen levels based on said received signal and to correlate and to simultaneously display the patient's turn angle relative to the horizontal, thereby allowing correlation between the patient's blood-oxygen levels and the patient's turn angle.

8. The patient interface system of claim 7, further comprising:

a universal port; and wherein said processor is further adapted to (a) sense a plurality of signals received at said universal port, (b) process such signals to distinguish identifiable signals amongst such plurality of signals, (c) correlate such identifiable signals with identifying profiles, and (d) process such plurality of signals based on data related to a particular profile.

9. The patient interface system of claim 7, wherein said processor is further adapted to control a patient turning device in response to the blood-oxygen level signal.

10. The patient interface system of claim 7, wherein said processor is further adapted to generate a suggested kinetic therapy regimen, the suggested kinetic therapy regimen being based upon the received blood-oxygen level signal.

11. The patient interface system of claim 10, wherein said processor is further adapted to control a patient turning device according to the suggested kinetic therapy regimen.

12. The patient interface system of claim 11, wherein said processor is further adapted to initiate control of patient turning in response to an input made at said display screen.

13. The patient interface system of claim 10, wherein:

said electronic connection port is a universal port adapted to operatively receive any one of a plurality grouping of conventional blood-oxygen transducer leads; and said processor is further adapted to (a) process the received blood-oxygen level signal to distinguish an identifiable component of the received blood-oxygen level signal, (b) correlate such identifiable component with an identifying profile, and (c) process the received blood-oxygen level signal based on data related to the identifying profile.

14. A patient interface system, said system comprising:

a bed for supporting a patient, said bed comprising a receiving port for operatively receiving port adapted to operatively receive a conventional transducer lead connector, the connector being adapted to cooperate with a conventional transducer to provide a signal related to a sensed physiological characteristic of the patient; and an outgoing port in communication with said receiving port, said outgoing port being adapted to releasably cooperate with a conventional electrical lead for transmitting signals received by said receiving port and communicated to said outgoing port.

* * * * *